(12) United States Patent
Gadelle et al.

(10) Patent No.: US 6,559,135 B2
(45) Date of Patent: May 6, 2003

(54) PER-(3-6-ANHYDRO)CYCLODEXTRINS DERIVATIVES, PREPARATION AND USE THEREOF FOR SEPARATING IONS

(75) Inventors: Andrée Gadelle, Montbonnot (FR); Florence Fauvelle, Grenoble (FR); Jean-Claude Debouzy, La Terrasse (FR)

(73) Assignees: Commissariat a l'Energie Atomique, Paris (FR); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 09/926,637
(22) PCT Filed: Mar. 27, 2001
(86) PCT No.: PCT/FR01/00923
§ 371 (c)(1), (2), (4) Date: Nov. 28, 2001
(87) PCT Pub. No.: WO01/72849
PCT Pub. Date: Oct. 4, 2001

(65) Prior Publication Data
US 2002/0137923 A1 Sep. 26, 2002

(30) Foreign Application Priority Data
Mar. 28, 2000 (FR) .............................. 0003899

(51) Int. Cl.⁷ ..................... A61K 31/715; C08B 37/16
(52) U.S. Cl. .................. 514/58; 536/103; 536/124
(58) Field of Search ................ 514/58; 536/103, 536/124

(56) References Cited

U.S. PATENT DOCUMENTS 5,792,857 A  8/1998  Baudin et al. .............. 536/103

FOREIGN PATENT DOCUMENTS

| EP | 0 787 744 | 8/1997 |
| FR | 2 764 525 | 12/1998 |
| WO | WO 98/56829 | 12/1998 |
| ZA | 985079 | 6/1998 |

OTHER PUBLICATIONS

P. R. Ashton, et al., Angew. Chem. Int. Ed. Engl., vol. 30, No. 1, pp. 80–81, "Synthesis and Characterization of Per-3, –6–Anhydro Cyclodextrins", 1991.

D. Duchene, et al., Cyclodextrins and their Industrial Uses, Chapter 6, pp. 211–257, "Pharmaceutical Applications of Cyclodextrins", 1987.

A. Gadelle, et al., Angew. Chem. Int. Ed. Engl., vol. 30, No. 1, pp. 78–80, "Selective Halogenation at Primary Positions of Cyclomaltooligosaccharides and a Synthesis of Per–3, 6–Anhydro Cyclomaltooligosaccharides", 1991.

H. Yamamura, et al., Tetrahedron Letters, vol. 36, No. 7, pp. 1093–1094, "Synthesis and Alkali Metal Ion Binding of Poly(3,6–Anhydro)–α–Cyclodextrins", 1995.

H. Yamamura, et al., Chem. Pharm Bull., vol. 39, No. 10, pp. 2505–2508, "Preparation of Heptakis (6–O–(p–Tosyl))–β–Cyclodextrin and Heptakis(6–O–(p–tosyl)–2–O–(p–Tosyl)–β–Cyclodextrin and Their Conversion to Hepatakis(3, 6–Anhydro)–β–Cyclodextrin", Oct. 1991.

H. Yamamura, et al., J. Chem. Soc., Chem. Commun., pp. 636–637, "Preparation of Octakis (3,6–Anhydro)–γ–Cyclodextrin and Characterization of Its Cation Binding Ability", 1993.

C. H. Evans, Biochemistry of the Lanthanides, Plenum Press, pp. 211–283, "Interactions of Lanthanides With Tissues, Cells, and Cellular Organelles", 1990.

*Primary Examiner*—Kathleen K. Fonda
*Assistant Examiner*—Leigh C. Maier
(74) *Attorney, Agent, or Firm*—Oblon, Spivak, McClelland, Maier & Neustadt, P.C.

(57) ABSTRACT

The invention concerns derivatives of per-(3,6-anhydro)-cyclodextrin, their preparation, and their use in separating polluting ions, for example in human decontamination. These derivatives correspond to one of the following formula:

(I) and (II)

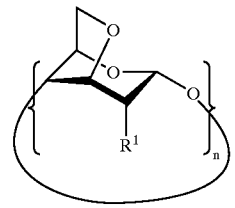

(I)

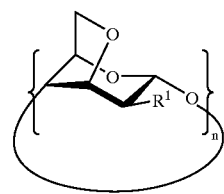

(II)

in which at least one of the $R^1$ groups represents the group —$OCH_2COOH$ and the other $R^1$ groups, which may be identical or different, represent a group that corresponds to one of the following formula: OH, $OR^2$, SH, $SR^2$, $OCOR^2$, $NH_2$, $NHR^2$, $NR^2R^3$, $CONH_2$, $CONHR^2$, $CONR^2R^3$, CN, $COOR^2$, COOH and $R^2$, in which $R^2$ and $R^3$, which may be identical or different, represent an aliphatic or aromatic hydrocarbon group, either saturated or unsaturated, which may include one or several hetero-atoms comprising O, S and N, and n is equal to 6, 7 or 8.

15 Claims, 2 Drawing Sheets

PER-(3-6-ANHYDRO)CYCLODEXTRINS DERIVATIVES, PREPARATION AND USE THEREOF FOR SEPARATING IONS

This application is the national stage entry of PCT/FR01/00923, filed Mar. 27, 2001.

TECHNICAL FIELD

The present invention concerns new derivatives of per-(3,6-anhydro)-cyclodextrin, which may be used, in particular, for fixing and separating ions, such as ions of cobalt, the lanthanides and uranyl.

It may, in particular, be applied to the field of environmental decontamination, and human decontamination, of these polluting ions.

STATE OF THE PRIOR ART

Cyclodextrins or cyclo-malto-oligosaccharides are compounds that occur naturally, formed from chains of α-linked (1,4) glucose groups.

Extensive studies have shown that these compounds are capable of forming inclusion complexes with hydrophobic molecules, which allow them to be rendered soluble in aqueous media. Numerous applications have been proposed to take advantage of this phenomenon, particularly in the pharmaceutical field, as described by D. Duchêne in "Pharmaceutical application of cyclodextrins" in "Cyclodextrins and their industrial uses". D. Duchêne, Ed., Editions de Santé, Paris, 1987, pages 213–257 (I).

Pharmaceutical specialities have already been commercialised in Japan, in Italy and, more recently, in France, in the form of complexes in cyclodextrins. In France, the first active ingredient marketed in the form of an inclusion complex in a cyclodextrin is Piroxicam, an anti-inflammatory sold by Pierre Fabre Médicament, under the trade name BREXIN®. Amongst the very many modified derivatives of these cyclodextrins, those in which the cavity is turned round itself have interesting properties, even though their ability to include organic molecules is lost or very limited. Compounds of this type are per-(3,6-anhydro)-cyclodextrins.

The synthesis of these per-anhydro-cyclodextrins was initially described in 1991 in document (2): A. Gadelle and J. Defaye, Angew. Chem. Int. Ed. Engl., (1991), 30, pages 78–79; and document (3): P. R. Ashton, P. Ellwood, I. Staton and J. F. Stoddart, Angew. Chem. Int. Ed. Engl., (1991), 30, pages 80–81, and it has been demonstrated that these derivatives have favourable solubility in water as well as in organic solvents. Some later studies (document (4): H. Yamamura and K. Fujita, Chem. Pharm. Bull., (1991), 39, pages 2505–2508; document (5): H. Yamamura, T. Ezuka, Y. Kawase, M. Kawai, Y. Butsugan and K. Fujita, J. Chem. Soc., Chem. Com., (1993), pages 636–637; and document (6): H. Yamamura, H. Nagaoka, M. Kawai and Y. Butsugan, Tetrahedron Lett. (1995), 36, pages 1093–1094) have, moreover, shown that these per-anhydro derivatives can complex alkaline ions with quite significant selectivity.

Document FR-A-2 744 127 (7) and document FR-A-2 764 525 (8) describe other derivatives of per-(3,6-anhydro)-cyclodextrins substituted in position 2, which are useful for the separation of different ions, and in particular potassium and caesium in the case of document (7), thanks to the presence of an acetyl substituent, or lead in the case of document (8), thanks to the presence of a methyl substituent.

However, it is not possible to obtain satisfactory separation by complexation of ions of cobalt, uranyl and the lanthanides, such as dysprosium, which pollute the environment, with the derivatives described in these documents.

Moreover, the lanthanide ions are toxic to living organisms because they disrupt calcium and sodium ionic exchanges. Thus, lanthane, which is the same size as calcium but which does not have the same valency, disrupts exchanges, as described by C. H. Evans in "Interactions of Lanthanides with Tissues, Cells and Cellular Organelles" in Biochemistry of the Lanthanides, C. H. Evans Ad., Plenum Press, New York, 1990, pp. 211–283 (9).

DESCRIPTION OF THE INVENTION

The present invention precisely concerns new derivatives of per-anhydro-cyclodextrins in which the substituent in the 2 position is selected to provide them with properties for complexing polluting ions such as $Co^{2+}$, $UO_2^{2+}$ and the lanthanide ions such as $Dy^{3+}$ and $Eu^{3+}$.

According to the invention, the derivative of per-(3,6-anhydro)-cyclodextrin corresponds to one of the following formulae:

(I) and (II)

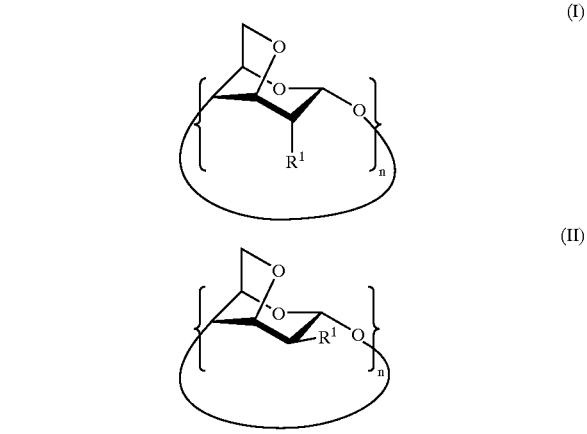

in which at least one of the $R^1$ groups represents the group —$OCH_2COOH$ and the other $R^1$ groups, which may be identical or different, represent a group that corresponds to one of the following formulae: OH, $OR^2$, SH, $SR^2$, $OCOR^2$, $NH_2$, $NHR^2$, $NR^2R^3$, $CONH_2$, $CONHR^2$, $CONR^2R^3$, CN, $COOR^2$, COOH and $R^2$, in which $R^2$ and $R^3$, which may be identical or different, represent an aliphatic or aromatic hydrocarbon group, either saturated or unsaturated, which may include one or several hetero-atoms comprising O, S and N, and n is equal to 6, 7 or 8.

In the cyclodextrin derivative with formula (I) or (II), the aliphatic or aromatic hydrocarbon groups that may be used for $R^2$ and $R^3$ may be different types. They are composed of a carbon chain in which certain carbon atoms may be replaced by one or several hetero-atoms such as O, S and N, and they can include one or several ethylenic or acetylenic unsaturated groups. Furthermore, the hydrocarbon group may comprise various substituents, in particular functional groups or halogen atoms. The aromatic hydrocarbon groups may be composed of a phenyl or a tosyl group, which may be substituted, for example by alkyl groups with between 1 and 20 carbon atoms.

$R^2$ and $R^3$ may, in particular, represent a linear or branched alkyl group with between 1 and 20 carbon atoms.

According to a preferred embodiment of the invention, the derivative of per-(3,6-anhydro)-cyclodextrin is a derivative of α-cyclodextrin, in other words, where n=6 in the formulae (I) and (II) given above.

Even more preferably, the derivative used corresponds to formula (I), in which all of the $R^1$ groups represent the group —$OCH_2COOH$ and n is equal to 6.

The cyclodextrin derivatives according to the invention may be prepared by various procedures.

When the cyclodextrin derivative corresponds to formulae (I) or (II) given above, in which at least one of the $R^1$ groups represents the group —$OCH_2COOH$ and the other $R^1$ groups represent OH or another group and n is equal to 6, 7 and 8, these may be prepared by a procedure comprising the following stages:

1) reacting a per-anhydro-cyclodextrin, which corresponds to one of the formulae:
(III) or (IV)

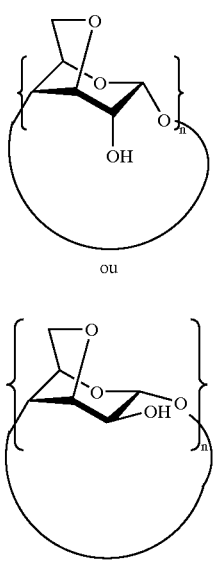

in which n is equal to 6, 7 or 8, with a alkali metal hydride, in order to convert the OH group(s) into OM group(s), where M represents an alkali metal;

2) reacting, in an alkaline medium, the modified per-anhydro-cyclodextrin obtained in 1) with a halide with the formula $XCH_2COOR^4$, in which X represents a halogen atom such as Cl, and $R^4$ represents H, $Si(CH_3)_3$ or an alkali metal, in sufficient quantity to ensure that at least one of the OM group(s) is converted into a —$CH_2COOR^4$ group;

3) reacting, in the case where all of the OM groups have not been converted into —$OCH_2COOR^4$ groups, the remaining OM groups with one or several reagents in order to convert them into $R^1$ groups that are intentionally different to —$OCH_2COOH$; and 4) treating the derivative of per-anhydro-cyclodextrin obtained in 3) with an alcohol, water or a slightly acid medium in order to convert the —$OCH_2COOR^4$ groups into —$OCH_2COOH$ groups.

In order to carry out stage 2), sufficient $XCH_2COOR^4$ is used to modify one or several of the OH groups in the cyclodextrin.

In stage 4), when $R^4$ represents M, the —$OCH_2COOR^4$ groups are converted into —$OCH_2COOH$ groups through the action of an alcohol such as methanol. Water may also be used, but the reaction is more violent.

When $R^4$ represents $Si(CH_3)_3$, a slightly acid medium is used to regenerate the acid function.

When the cyclodextrin derivative corresponds to formulae (I) or (II) given above, in which the other $R^1$ groups represent $OR_2$, where $R^2$ has the signification given above, the same procedure described previously is followed in order to introduce the —$OCH_2COOM$ groups, then the derivative is reacted with a halide with the formula $R^2X$, in which $R^2$ has the signification given above, and X is a halogen atom.

When the cyclodextrin derivative corresponds to formulae (I) or (II), in which the other $R^1$ groups represent $OCOR^2$, the same procedure described previously is followed in order to introduce, firstly, the —$OCH_2COOM$ groups, then the resulting derivative is reacted with a halide or acid anhydride with the formulae $R^2COX$ or $(R^2CO)_2O$, in which $R^2$ has the signification given above, and X is a halogen atom, in order to replace the remaining hydroxyl groups by $OCOR^2$ groups.

When one wishes to prepare a cyclodextrin derivative in which the other $R^1$ group(s) represent a halogen atom or a group with the formulae SH, $SR^2$, $NH_2$, $NR^2R^3$, $CONR^2R^3$, $CONH_2$, CN, $COOR^2$, COOH, or $R^2$, where $R^2$ and $R^3$ have the signification given above, and where n is equal to 6, 7 or 8, one can carry out the following stages, starting with a partially modified per-anhydro-cyclodextrin, in other words, one in which at least one of the $R^1$ groups represents —$OCH_2COOH$ and the other $R^1$ groups represent OH, and by carrying out the following stages:

1) reacting this per-anhydro-cyclodextrin with an alkali metal halide in order to convert the OH group(s) into OM group(s), where M represents an alkali metal;

2) reacting the modified per-anhydro-cyclodextrin obtained in 1) with a chloride that corresponds to the formula $ClSO_2R^2$, where $R^2$ has the signification given above, in order to obtain the derivative that corresponds to formulae (I) or (II), in which at least one of the $R^1$ groups is a group with the formula $OSO_2R^2$; and 3) reacting the derivative obtained in stage 2) with one or several appropriate reagents in order to replace the $OSO_2R^2$ group by the desired $R^1$ group.

In this procedure, the per-(3,6-anhydro)-cyclodextrin is firstly converted into an alcoholate through the action of an alkali metal hydride, then this alcoholate is converted into the derivative comprising a group initially with the formula $OSO_2R^2$, which is then reacted, in one or several stages, with one or several appropriate reagents in order to replace this initial group by the desired $R^1$ group.

Thus, in the case where it is desired that $R^1$ represents $NH_2$, the compound described in stage 2) may be reacted with $N_3M$. The compound obtained in this manner, called an azide, can be subjected to catalytic hydrogenation or be treated with ammonia $NH_3$, in order to obtain the product where $R^1$ represents $NH_2$.

In the case where it is desired that $R^1$ represents $NHR^2$ or $NR^2R^3$, the product may be obtained by reacting the compound described in stage 2) with $NH_2R^2$ or $NHR^2R^3$.

In the case where it is desired that $R^1$ represents SH or $SR^2$, the compound described in stage 2) may be reacted with a halide $X^-$, which gives the compound where ($R^1$=X), and which is then reacted with $HS^-$ or $R^2S^-$, in order to give a compound where $R^1$ represents SH or $SR^2$.

In the case where it is desired that $R^1$ represents a hydrocarbon group, $R^1{}_2LiCu$ (where $R^1$ represents a hydrocarbon group) is used to give a final compound where $R^1$ then represents a hydrocarbon group.

In the same way, the compound where $R^1$ represents a halogen may be reacted with $CN^-$ in order to give a final compound where $R^1$ represents CN.

In the same way, the compound where $R^1$ represents CN may, through partial controlled hydrolysis, give a compound where $R^1$ represents $CONH_2$. The compound where $R^1$ represents CN may, through complete hydrolysis, give a compound where $R^1$ represents COOH.

The compound where $R^1$ represents COOH may, through esterification, give a compound where $R^1$ represents $COOR^2$.

The compound where $R^1$ represents COOH may be reacted with $NHR^2R^3$ or $NH_2R^2$ in the presence of DCC (dicyclohexyl carbodiimide) in order to give a compound where $R^1$ represents $NR^2R^3$ or $NH_2R^2$.

The per-(3,6-anhydro)-cyclodextrin derivatives according to the invention may be used, in particular, for fixing or separating ions.

Thus, another object of the invention is a process for fixing or separating ions, which consists in bringing into contact a medium containing the said ions with a derivative of per-(3,6-anhydro)-cyclodextrin that corresponds to one of the following formulae:

(I) and (II)

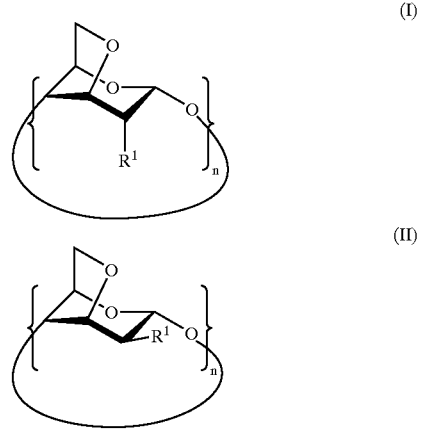

in which at least one of the $R^1$ groups represents the group $-OCH_2COOH$ and the other $R^1$ groups, which may be identical or different, represent a group that corresponds to one of the following formulae: OH, $OR^2$, SH, $SR^2$, $OCOR^2$, $NH_2$, $NHR^2$, $NR^2R^3$, $CONHR^2$, $CONR^2R^3$, $CONH_2$, CN, $COOR^2$, COOH and $R^2$, in which $R^2$ and $R^3$, which may be identical or different, represent an aliphatic or aromatic hydrocarbon group, either saturated or unsaturated, which may include one or several hetero-atoms comprising O, S and N, and n is equal to 6, 7 or 8, in order to fix the said ions in the form of a complex with the per-(3,6-anhydro)-cyclodextrin derivative and separating them from the said medium.

Various types of ions may fixed or separated by the process according to the invention; they may, for example, be ions of the actinides, such as uranyl, the lanthanides or of polluting metals such as cobalt.

The process according to the invention applies, in particular, to the separation and fixing of cobalt and the lanthanide ions in the form of complexes.

In fact, cobalt, the lanthanides, and their derivatives pollute the environment and are toxic to both humans and animals. The main toxicological effects are on neurological development and the correct working of the nervous system. It is therefore necessary to separate and eliminate these ions from the environment and to store them in a safe manner.

In addition, products that could ensure decontamination of cobalt and the lanthanides in living organisms, while preventing them acting on the nervous system and on other organs, would be of great interest in resolving these problems.

According to the invention, it has been found that derivatives of per-(3,6-anhydro)-cyclodextrin, which correspond to the formulae (I) and (II) given above, have high specificity for cobalt and the lanthanides, and are capable of complexing with them, with yields that can reach 100%, even in the presence of other ions, such as sodium ions.

In this manner, it is possible to separate cobalt and the lanthanides from the environment in the form of complexes.

Thus, another object of the invention concerns metal complexes chosen from Dy, Eu, Lu, La and Co and derivatives of per-(3,6-anhydro)-cyclodextrin that correspond to the formulae (I) and (II) described above.

In order to implement the ion separation process according to the invention, the derivatives of per-(3,6-anhydro)-cyclodextrin, which correspond to formulae (I) or (II), may be used in the form of an aqueous solution or organic solution.

When the medium containing the ions that need to be separated or fixed is an aqueous solution, the derivative of cyclodextrin may be dissolved in an organic solvent that is immiscible with the aqueous solution, for example in chloroform, in order to form the complex in the organic solution and to separate it easily from the aqueous solution.

The cyclodextrin derivative may also be used in an aqueous solution, particularly when decontaminating living organisms.

In fact, it is known that cyclodextrin derivatives with the formulae (I) or (II) are bio-compatible compounds. They may therefore be administered to humans or animals in order to fix cobalt or the lanthanides in the form of complexes and thus avoid them interacting with the body organs of humans or animals.

Thus, another object of the invention concerns a pharmaceutical composition for the decontamination of the lanthanides and cobalt from living organisms, whereby it comprises a derivative of per-(3,6-anhydro)-cyclodextrin that corresponds to one of the formulae (I) and (II) described above and a pharmaceutically acceptable carrier.

Preferably, the derivative of per-(3,6-anhydro)-cyclodextrin used in this composition corresponds to formula (I), in which all of the $R^1$ groups represent the group $-OCH_2COOH$ and n is equal to 6.

This composition may be administered orally or by injection.

The aqueous solutions may contain up to 0.08 mol/l of the derivative corresponding to formula (I).

The quantities administered will depend on the level of contamination and the body weight of the patient.

The cyclodextrin derivatives according to the invention have numerous advantages. In particular, when they are per-substituted, in other words when all of the $R^1$ groups are different to the group OH, the derivatives have good solubility in organic solvents such as chloroform, acetone, tetrahydrofuran, etc. This solubility is valuable when they are used in ionic separation, since it allows the separation to be carried out by liquid-liquid exchanges, which are well known to those skilled in the art.

Furthermore, the possibility of introducing one or several specific chemical groups enables complexing agents to be made to measure for a wide variety of ions. This facility is, moreover, amplified by the fact that the three natural cyclodextrins that may be used as raw materials have different cavity diameters, which can thus provide additional selectivity as regards the size of the ions to be separated.

The initial products with formulae (III) or (IV) used in the invention can be prepared by conventional procedures, such as those described in documents (2) by A. Gadelle et al. and (3) by P. R. Ashton et al. cited above.

Other characteristics and advantages of the invention will become clearer from the description of the examples that follow, which are given by way of illustration and are in no way limiting, while referring to the drawings given in the Appendices.

DETAILED DESCRIPTION OF THE EMBODIMENTS

EXAMPLE 1

Preparation of Hexakis-(3,6-anhydro-2-O-carboxymethyl)-cyclomaltohexaose

This compound corresponds to formula (I) given above, in which all of the $R^1$ groups represent —$OCH_2COOH$ groups and n is equal to 6.

1 g (1.15 mmol) of hexakis-(3, 6-anhydro)-cyclomaltohexaose, dried under vacuum for 2 hours at 120° C., is weighed out and 10 ml of anhydrous dimethyl sulphoxide (DMSO) and 10 ml of a solution of DMSO that has reacted with sodium hydride (a 2 N solution of sodium hydride in DMSO) are added. The solution is maintained under agitation and under an argon blanket at ambient temperature for 3 hours. A blue grey solution is obtained. Then, sodium mono-chloroacetate (1.6 g, 14 mmol) is added. The solution is stored at ambient temperature for 24 hours, then the argon flow is cut off. The solution is then treated with 10 ml of methyl alcohol, which has been thoroughly dried, taken up in acetone and filtered. The resulting powder, dissolved in water, is neutralised with hydrochloric acid (1 N solution), and dialysed against water for 24 hours (Spectra/Port®CE Sterile DispoDialysers®— with a membrane made out of cellulose ester—MWCO 500). The reaction is quantitative. The dialysat is lyophilised and characterised by proton and carbon nuclear magnetic resonance spectrometry.

Figure 1:
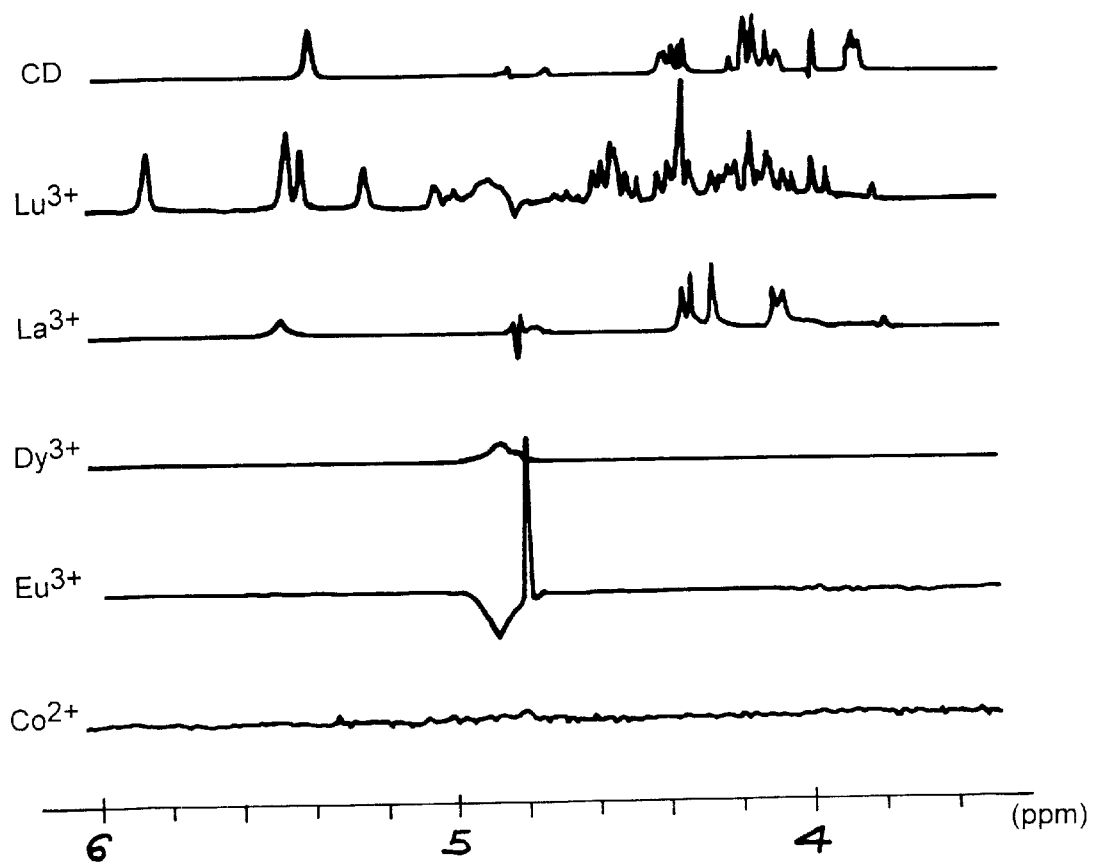
FIG. 1 shows the proton nuclear magnetic resonance (NMR) spectra of the derivative of example 1 on its own (CD), in solution at a concentration of 1 mmol/l, or in the presence of 4 mmol/l of $Lu^{3+}$, $La^{3+}$, $Dy^{3+}$, $Eu^{3+}$ and $Co^{2+}$.

FIG. 1 shows the proton NMR spectrum of this product (CD).

The product is then used as such for the complexing applications outlined in the following examples.

EXAMPLE 2

Preparation of Complexes of Hexakis-(3,6-anhydro-2-O-carboxymethyl)-cyclomaltohexaose Each complex is prepared by adding 4 mmol/l of the tested cation to 500 µl of an aqueous solution containing 1 mmol/l of the product from Example 1. The following cations were tested: $Lu^{3+}$, $La^{3+}$, $Dy^{3+}$, $Eu^{3+}$ and $Co^{2+}$.

The resulting complexes were then characterised by proton nuclear magnetic resonance spectrometry. The spectra obtained for $Lu^{3+}$, $La^{3+}$, $Dy^{3+}$, $Eu^{3+}$ and $Co^{2+}$ are shown in FIG. 1.

If these spectra are compared with the spectrum of the product from Example 1 on its own (CD), it can be seen that the spectra are considerably modified by the addition of the tested cations.

In the case of $Dy^{3+}$, $Eu^{3+}$ and $Co^{2+}$ ions, there is a very strong interaction between these ions and the peracid. In fact, the spectrum of the per-(3,6-anhydro)-cyclodextrin derivative has completely disappeared, indicating that the protons involved in the interaction have been completely immobilised.

In the case of lanthane, the H6 and H6' protons located on the anhydro bridge can still be observed.

The case of lutetium is even more complex: the spectrum of the cyclodextrin becomes very complicated with the appearance of a multitude of peaks that cannot be directly attributed. It is likely that several stoichiometrically different complexes co-exist in solution.

EXAMPLE 3

In this example, experiments were carried out to compare the derivative from Example 1 and ethylene diamine tetra acetate (EDTA) in complexing $Dy^{3+}$, $Eu^{3+}$ and $Co^{2+}$ ions, in order to get an idea of the force of the complexes prepared in Example 2.

With this in mind, 4 mmol/l of the tested cation and EDTA were added to 50 µl of an aqueous solution containing 1 mmol/l of the derivative from Example 1. The resulting products were than characterised by proton NMR spectrometry.

Figure 2:
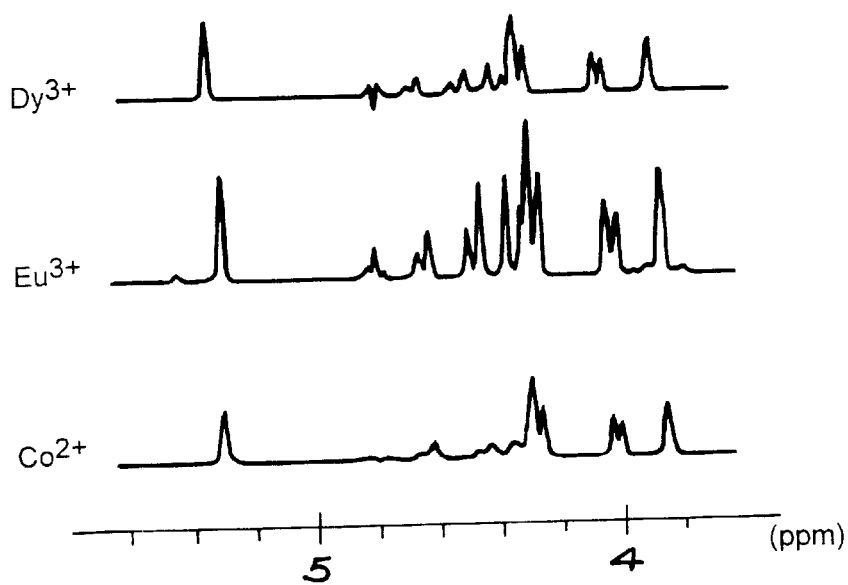
FIG. 2 shows the NMR proton spectra of the derivative of example 1 in solution at a concentration of 1 mmol/l, in the presence of ethylene diamine tetra-acetate and 4 mmol/l of $Dy^{3+}$, $Eu^{3+}$ and $Co^{2+}$.

The spectra obtained are shown in FIG. 2. In this figure, it can be seen that the addition of EDTA makes it possible, in all cases, to partially recover the cyclodextrin spectrum. However, despite the addition of a large excess of EDTA compared to the cyclodextrin, the cyclodextrin spectrum is not completely recovered. This demonstrates that the cyclodextrin derivative complexes the cations more strongly than EDTA.

EXAMPLE 4

In this example, the complexation properties of the derivative from Example 1 were tested vis à vis physiological cations: calcium, sodium and potassium, all of which are required in the development of living organisms.

In fact, for human decontamination applications, the derivative must not complex with the physiological cations.

The same procedure was used as given in Example 2, and the resulting products were characterised by proton NMR spectrometry.

Figure 3:
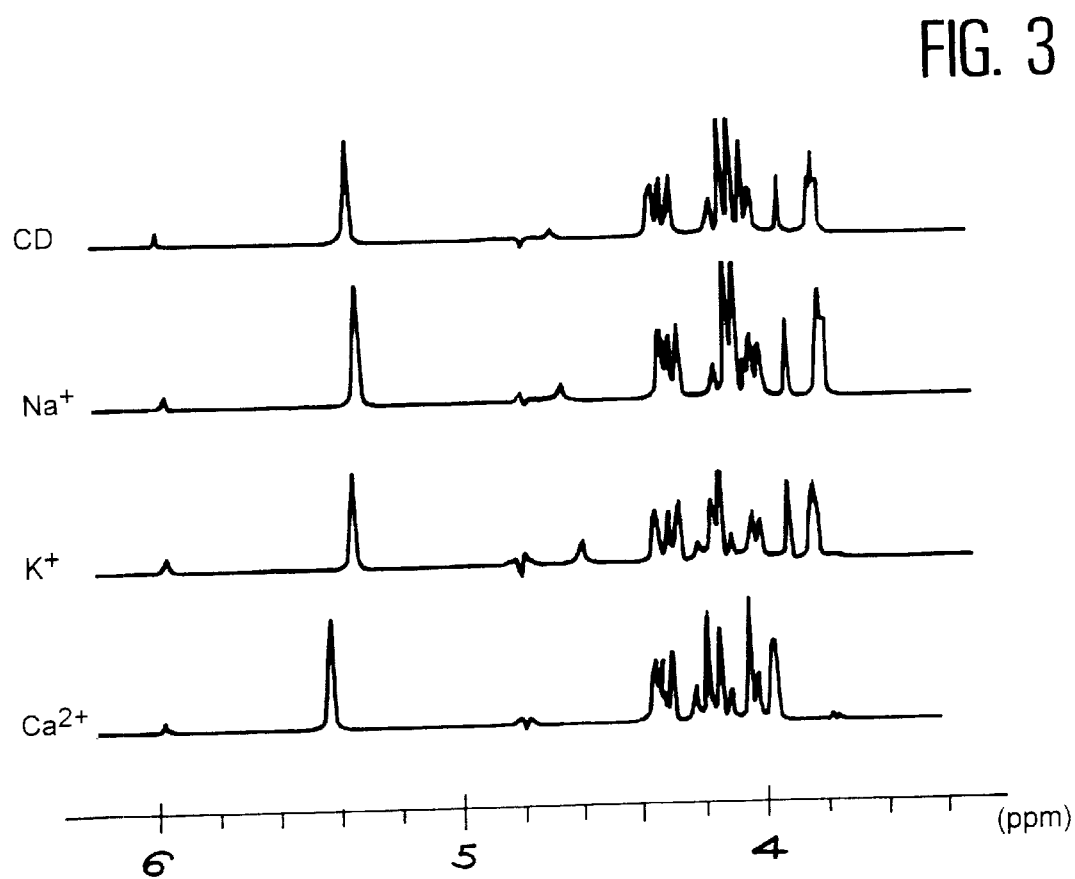
FIG. 3 shows the proton NMR spectra of the derivative of example 1 on its own (CD) and in the presence of the physiological cations $Na^+$, $K^+$ and $Ca^{2+}$.

FIG. 3 shows the results obtained with $Na^+$, $K^+$ and $Ca^{2+}$.

In this figure, the spectrum (CD) corresponds to the derivative from Example 1 on its own.

It can thus be seen that the peaks from the derivative from Example 1 are hardly affected by the presence of the physiological cations, compared to the spectra shown in FIG. 1.

LIST OF DOCUMENTS CITED (1): D. Duchêne "Pharmaceutical application of cyclodextrins" in "Cyclodextrins and their industrial uses", D. Duchêne, Ed., Editions de Santé, Paris, 1987, pages 213–257.

(2): A. Gadelle and J. Defaye, Angew. Chem. Int., Ed. Engl., 1991, 30, pages 79–79.

(3): P. R. Ashton, P. Ellwood, I. Staton and J. F. Stoddard, Angew. Chem. Int., Ed. Engl., 1991, 30, pages 80–81.

(4): H. Yamamura and K. Fujita, Chem. Pharm. Bull., 1991, 39, pages 2505–2508.

(5): H. Yamamura, T. Esuka, Y. Kawase, M. Kawai, Y. Butsugan and K. Fujita, J. Chem. Soc., Chem. Commun., 1993, pages 636–637.

(6) H. Yamamura, H. Nagaoka, M. Kawai and Y. Butsugan, Tetrahedron Lett., 1995, 3b, pages 1093–1094.

(7): FR-A-2 744 124

(8): FR-A-2 764 525

(9): C. H. Evans "Interactions of Lanthanides with Tissues, Cells and Cellular Organelles", in Biochemistry of the Lanthanides, C. H. Evans, Ad., Plenum Press, New York, 1990, pages 211–283.

What is claimed is:

1. Derivative of per-(3,6-anhydro)-cyclodextrin that corresponds to one of the following formulae:

(I) and (II)

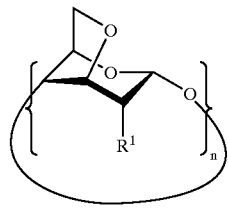

(I)

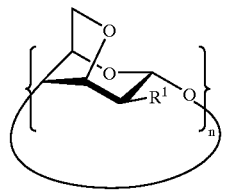

(II)

in which at least one of the $R^1$ groups represents the group —$OCH_2COOH$ and the other $R^1$ groups, which may be identical or different, represent a group that corresponds to one of the following formulae: OH, $OR^2$, SH, $SR_2$, $OCOR^2$, $NH_2$, $NHR^2$, $NR^2R^3$, $CONH_2$, $CONHR^2$, $CONR^2R^3$, CN, $COOR^2$, COOH and $R^2$, in which $R^2$ and $R^3$, which may be identical or different, represent an aliphatic or aromatic hydrocarbon group, either saturated or unsaturated, which may include one or several hetero-atoms comprising O, S and N, and where n is equal to 6, 7 or 8.

2. Derivative of per-(3,6-anhydro)-cyclodextrin according to claim 1, in which all of the $R^1$ groups represent the group —$OCH_2COOH$ and n is equal to 6.

3. Process for preparing a derivative of per-(3,6-anhydro)-cyclodextrin that corresponds either to formula (I) or (II):

(I) and (II)

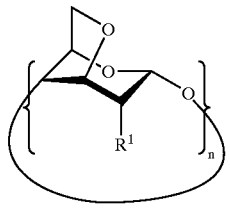

(I)

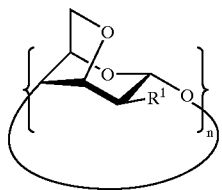

(II)

in which at least one of the $R^1$ groups represents the group —$OCH_2COOH$ and the other $R^1$ groups, which may be identical or different, represent a group that corresponds to one the following formulae: OH, $OR^2$, SH, $SR_2$, $OCOR^2$, $NH_2$, $NHR^2$, $NR^2R^3$, $CONH_2$, $CONHR^2$, $CONR^2R^3$, CN, $COOR^2$, COOH and $R^2$, in which $R^2$ and $R^3$, which may be identical or different, represent an aliphatic or aromatic hydrocarbon group, either saturated or unsaturated, which may include one or several hetero-atoms comprising O, S and N, and where n is equal to 6, 7 or 8, which comprises the following stages:

1) a per-anhydro-cyclodextrin that corresponds to the formula:

(III) or (IV)

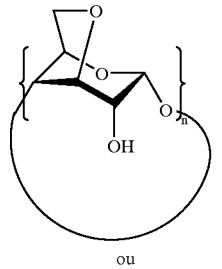

(III)

ou

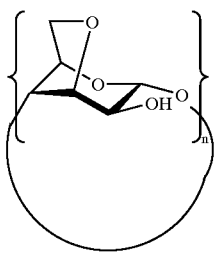

(IV)

in which n is equal to 6, 7 or 8, is reacted with an alkali metal hydride in order to convert the OH group(s) into OM group(s), where M represents an alkali metal;

2) reacting, in an alkaline medium, the modified per-anhydro-cyclodextrin obtained in 1) with a halide with the formula $XCH_2COOR^4$ in which X represents a halogen atom and $R^4$ represents H, $Si(CH_3)_3$ or an alkali metal, in sufficient quantity to ensure that at least one of the OM group(s) is converted into a $CH_2COOR^4$ group;

3) reacting, in the case where not all of the OM groups have been converted into —OCH$_2$COOR$^4$ groups, the remaining OM groups with one or several reagents in order to convert them into R$^1$ groups that are intentionally different to —OCH$_2$COOH; and 4) treating the derivative of per-anhydro-cyclodextrin obtained in 3) with an alcohol, a slightly acid medium or water in order to convert the —OCH$_2$COOR$^4$ groups into —OCH$_2$COOH groups.

4. Process for fixing or separating ions, consisting in bringing into contact a medium containing the said ions and a derivative of per-(3,6-anhydro)-cyclodextrin that corresponds to one of the following formulae:

(I) and (II)

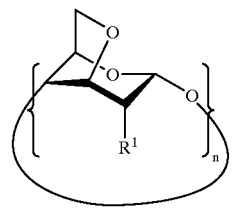

(I)

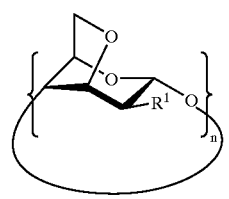

(II)

in which at least one of the R$^1$ groups represents the group —OCH$_2$COOH and the other R$^1$ groups, which may be identical or different, represent a group that corresponds to one of the following formulae: OH, OR$^2$, SH, SR$_2$, OCOR$^2$, NH$_2$, NHR$^2$, NR$^2$R$^3$, CONHR$_2$, CONR$^2$R$^3$, CONH$_2$, CN, COOR$^2$, COOH and R$^2$, in which R$^2$ and R$^3$, which may be identical or different, represent an aliphatic or aromatic hydrocarbon group, either saturated or unsaturated, which may include one or several hetero-atoms comprising O, S and N, and n is equal to 6, 7 or 8, in order to fix the said ions in the form of a complex with the derivative of per-(3,6-anhydro)-cyclodextrin, and separating them from the said medium.

5. Process according to claim 4, in which the said ions are ions of cobalt, the lanthanides and/or uranyl.

6. The process according to claim 5, wherein the derivative of per-(3,6-anhydro)-cyclodextrin corresponds to the formula (I), all of the R$^1$ groups represent the group —OCH$_2$COOH, and n is equal to 6.

7. Process according to claim 4, in which the said ions are ions of cobalt, dysprosium and/or europium.

8. The process according to claim 7, wherein the derivative of per-(3,6-anhydro)-cyclodextrin corresponds to the formula (I), all of the R$^1$ groups represent the group —OCH$_2$COOH, and n is equal to 6.

9. The process according to claim 4, wherein as the derivative of per-(3,6-anhydro)-cyclodextrin corresponds to the formula (I), in which all of the R$^1$ groups represent the group —OCH$_2$COOH and n is equal to 6.

10. The process according to claim 9, wherein the medium is an aqueous solution, and the derivative of per-(3,6-anhydro)-cyclodextrin is dissolved in an organic solvent that is immiscible with the aqueous solution.

11. The process according to claim 4, wherein the medium is an aqueous solution, and the derivative of per-(3,6-anhydro)-cyclodextrin is dissolved in an organic solvent that is immiscible with the aqueous solution.

12. The pharmaceutical composition for the decontamination of lanthanides and cobalt from living organisms, said composition comprising a derivative of per-(3,6-anhydro)-cyclodextrin that corresponds to one of the following formulae:

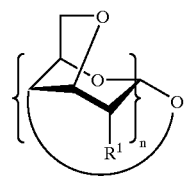

(I)

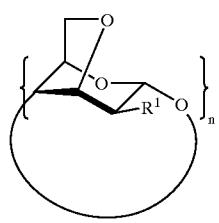

(II)

wherein at least one of the R$^1$ groups represents the group —OCH$_2$COOH and the other R$_1$ groups, which may be identical or different, represent a group that corresponds to one of the following formulae: OH, OR$^2$, SH, SR$^2$, OCOR$^2$, NH$_2$, NHR$^2$, NR$^2$R$^3$, CONR$^2$R$^3$, CONHR$^2$, CONH$_2$, CN, COOR$^2$, COOH and R$^2$, in which R$^2$ and R$^3$, which may be identical or different, represent an aliphatic or aromatic hydrocarbon group, either saturated or unsaturated, which may include one or several heteroatoms comprising O, S and N, and n is equal to 6, 7 or 8 and a pharmaceutically acceptable carrier.

13. The pharmaceutical composition according to claim 12, wherein the derivative of per-(3,6-anhydro)-cyclodextrin corresponds to the formula (I) in which all of the R$^1$ groups represent the group —OCH$_2$COOH, and n is equal to 6.

14. A complex of a metal chosen from Dy, Eu, Lu, La and Co and a derivative of per-(3,6-anhydro)-cyclodextrin that corresponds to one of the following formulae:

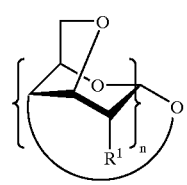

(I)

-continued

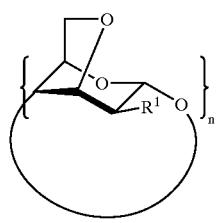
(II)

wherein
at least one of the $R^1$ groups represents the group —OCH$_2$COOH and the other $R^1$ groups, which may be identical or different, represent a group that corresponds to one of the following formulae: OH, OR$^2$, SH, SR$^2$, OCOR$^2$, NH$_2$, NHR$^2$, NR$^2$R$^3$, CONR$^2$R$^3$, CONHR$^2$, CONH$_2$, CN, COOR$^2$, COOH and R$^2$, in which R$^2$ and R$^3$, which may be identical or different, represent an aliphatic or aromatic hydrocarbon group, either saturated or unsaturated, which may include one or several heteroatoms comprising O, S and N, and n is equal to 6, 7 or 8.

15. The complex according to claim 14, wherein
the derivative of per-(3,6-anhydro)-cyclodextrin corresponds to the formula (I),
all of the $R^1$ groups represent the group —OCH$_2$COOH, and
n is equal to 6.

* * * * *